(12) United States Patent
Sharma et al.

(10) Patent No.: US 8,224,640 B2
(45) Date of Patent: *Jul. 17, 2012

(54) METHOD AND SYSTEM FOR COMPUTATIONAL MODELING OF THE AORTA AND HEART

(75) Inventors: Puneet Sharma, Rahway, NJ (US); Bogdan Georgescu, Plainsboro, NJ (US); Razvan Ioan Ionasec, Lawrenceville, NJ (US); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 49 days.

This patent is subject to a terminal disclaimer.

(21) Appl. No.: 12/825,905

(22) Filed: Jun. 29, 2010

(65) Prior Publication Data

US 2011/0060576 A1    Mar. 10, 2011

Related U.S. Application Data

(60) Provisional application No. 61/240,397, filed on Sep. 8, 2009.

(51) Int. Cl.
*G06F 19/00* (2011.01)
*G06F 17/10* (2006.01)
*G06G 7/58* (2006.01)
*G06K 9/00* (2006.01)

(52) U.S. Cl. ............... 703/19; 703/2; 703/11; 382/128

(58) Field of Classification Search .................. None
See application file for complete search history.

(56) References Cited

U.S. PATENT DOCUMENTS

| | | | |
|---|---|---|---|
| 7,117,026 B2 | 10/2006 | Shao et al. | |
| 7,450,780 B2 | 11/2008 | Roche et al. | |
| 2005/0281447 A1* | 12/2005 | Moreau-Gobard et al. | .. 382/130 |
| 2006/0004274 A1 | 1/2006 | Hawman | |
| 2006/0004275 A1 | 1/2006 | Vija et al. | |
| 2008/0101676 A1 | 5/2008 | Zheng et al. | |
| 2008/0262814 A1 | 10/2008 | Zheng et al. | |
| 2009/0123050 A1 | 5/2009 | Ionasec et al. | |
| 2010/0070249 A1* | 3/2010 | Ionasec et al. | .................. 703/2 |
| 2010/0280352 A1* | 11/2010 | Ionasec et al. | ............... 600/407 |

OTHER PUBLICATIONS

De Hart et al. Journal of Biomechanics (2003) vol. 36, pp. 103-112.*
Sermesant et al. Medical Image Analysis (2006) vol. 10, pp. 642-656.*
Deparis et al. (A Domain Decomposition Framework for Fluid-Structure Interaction Problems in Computational Fluid Dynamics (2004) Part I, pp. 41-58).*
Gerbeau et al. (2005) Computers and Structures, vol. 83:155-165.*
Scotti et al. (2007) Computers and Structures, vol. 85:1097-1113.*
Wang et al. (1999) IEEE Engineering in Medicine and Biology, Nov./Dec.: 33-39.*
Zhang et al. (2007) Comput. Methods Appl. Mech. Engrg., vol. 196:2943-2959.*
Ionasec, Razvan Ioan et al., "Dynamic Model-Driven Quantitative and Visual Evaluation of the Aortic Valve from 4D CT", Int'l Conference on Medical Image Computing and Computer-Assisted Intervention, 11(Pt 1), 2008.
Yang, Lin et al., "3D UltraSound Tracking of the Left Ventricles Using One-Step Forward Prediction and Data Fusion of Collaborative Trackers", CVPR, 2008.
Zheng, Yefeng, et al., "Four-Chamber Heart Modeling and Automatic Segmentation for 3D Cardiac CT Volumes Using Marginal Space Learning and Steerable Features", IEEE Transactions on Medical Imaging, 27(11), Nov. 2008.

* cited by examiner

*Primary Examiner* — Lori A Clow

(57) ABSTRACT

A method and system for generating a patient specific anatomical heart model is disclosed. A sequence of volumetric image data, such as computed tomography (CT), echocardiography, or magnetic resonance (MR) image data of a patient's cardiac region is received. A multi-component patient specific 4D geometric model of the heart and aorta estimated from the sequence of volumetric cardiac imaging data. A patient specific 4D computational model based on one or more of personalized geometry, material properties, fluid boundary conditions, and flow velocity measurements in the 4D geometric model is generated. Patient specific material properties of the aortic wall are estimated using the 4D geometrical model and the 4D computational model. Fluid Structure Interaction (FSI) simulations are performed using the 4D computational model and estimated material properties of the aortic wall, and patient specific clinical parameters are extracted based on the FSI simulations. Disease progression modeling and risk stratification are performed based on the patient specific clinical parameters.

25 Claims, 12 Drawing Sheets

FIG. 5
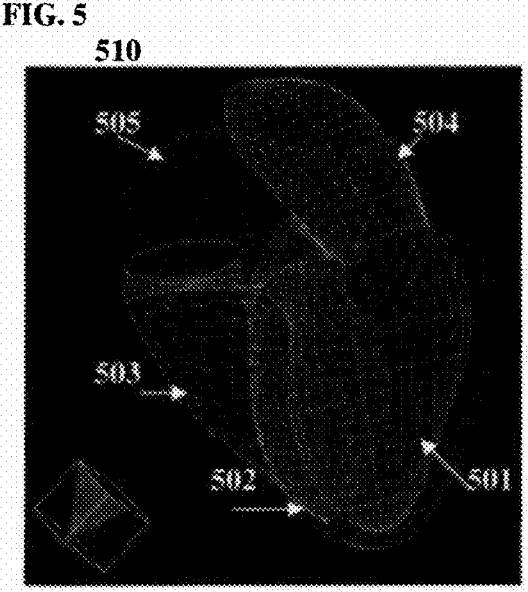
510
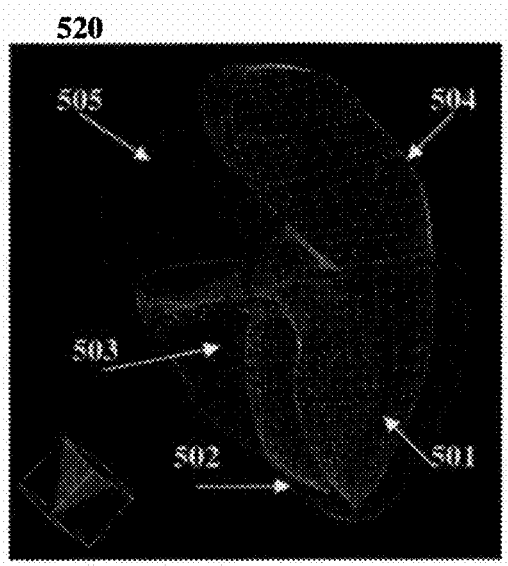
520
Diastole
Systole
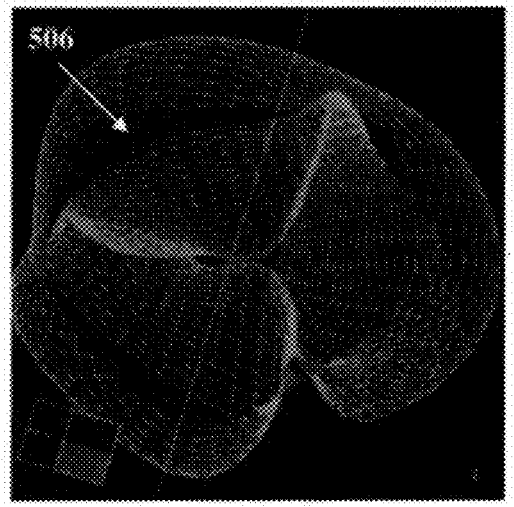
530
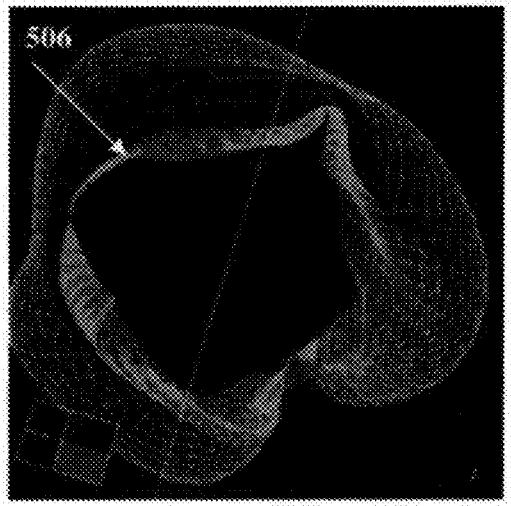
540

FIG. 6A
602
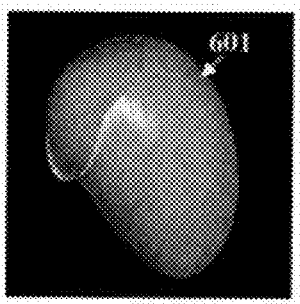
604
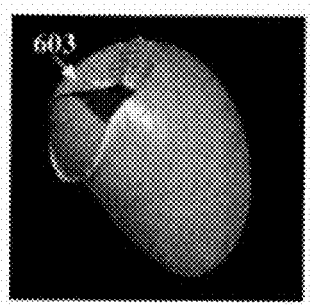
606
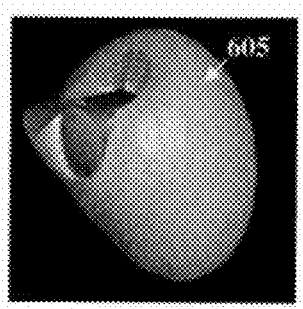
608
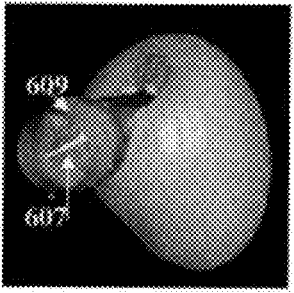
610
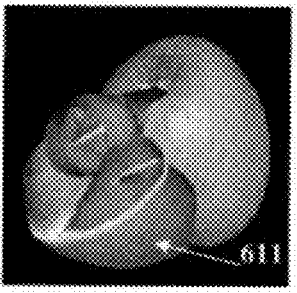
612
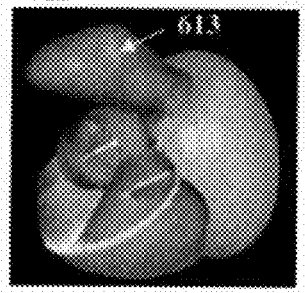
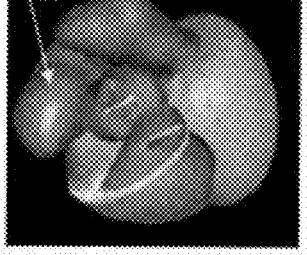
614
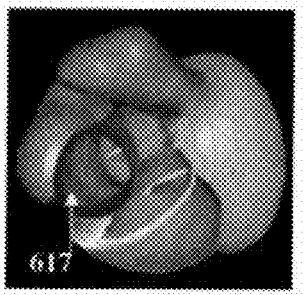
616
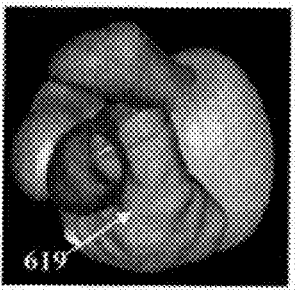
618

FIG. 6B
620
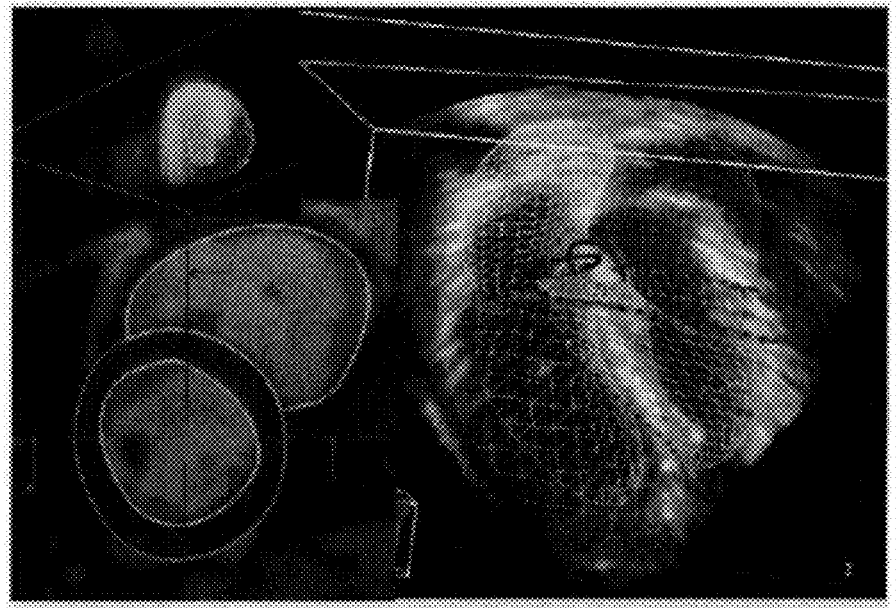
622
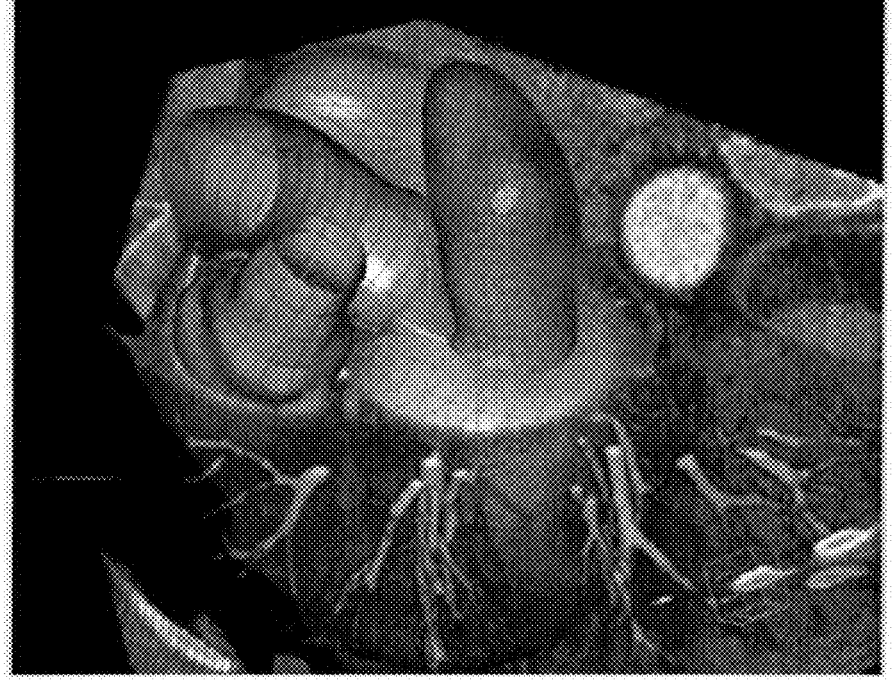

FIG. 7
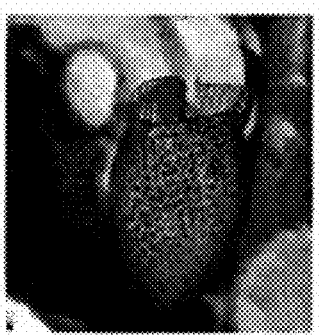  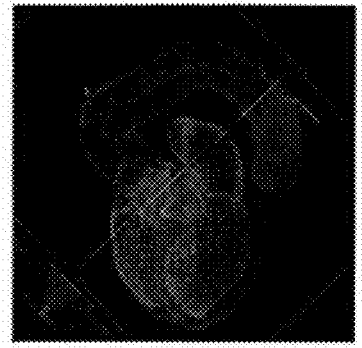
(a) (b) (c)

METHOD AND SYSTEM FOR COMPUTATIONAL MODELING OF THE AORTA AND HEART

This application claims the benefit of U.S. Provisional Application No. 61/240,397, filed Sep. 8, 2009, the disclosure of which is herein incorporated by reference.

BACKGROUND OF THE INVENTION

The present invention relates to modeling the heart in medical images, and more particularly, to modeling the heart using personalized 4D anatomical heart model of the full cardiac system estimated from volumetric image sequences for decision support in diagnosis and treatment of cardiac disease.

Cardiac disease is the leading cause of death for men and women in the United States and accounts no less than 30% of deaths worldwide. Although medical advances in recent years have provided important improvements in the diagnosis and treatment of complex cardiac diseases such as valvular disease, thoracic aortic aneurysm, and Tetralogy of Fallot, the incidence of premature morbidity and mortality is still large. These problems are due, at least in part, to a lack of accurate estimates (in-vivo and in-vitro) of patient-specific parameters that accurately characterize the heart and aortic anatomy, physiology and hemodynamics. As a result, early disease prediction and progression models are often based on generic data, rendering them ineffective for therapeutic interventions on individual patients.

In recent years, there have been significant advances in determining patient-specific geometry for the heart and other proximal structures using various medical imaging modalities, such as computed tomography (CT), magnetic resonance (MR), rotational X-ray, and Ultrasound. However, there has been little focus on extending the hemodynamic analysis by incorporating patient-specific geometry, boundary conditions, and material properties for the vascular structures. Hemodynamics and wall mechanics play a key role in the progression of cardiovascular diseases since the variations in mechanical loading on the endothelial and muscle cells have been attributed to changes in gene expression, and ultimately to disease onset and subsequent disease progression. The shear stress exerted on vessel walls (referred to as "wall shear stress") plays an important role in regulating some functions of the endothelium. The effect of age, hypertension, and other related cardio-vascular conditions (and associated defects) on the mechanical properties of the vascular wall is well established. Accordingly, a comprehensive patient-specific determination of the mechanical properties of the vascular wall is desirable.

BRIEF SUMMARY OF THE INVENTION

The present invention provides a method and system for decision support in treatment and prognosis of cardiac disease using a personalized anatomic model of the heart generated from volumetric image data. Embodiments of the present invention estimate patient specific material properties of the aortic wall using a non-linear, anisotropic, parametric, constitutive model for the mechanical properties of the aortic wall.

In one embodiment of the present invention, a multi-component patient specific 4D geometric model of the heart and aorta is estimated from a sequence of volumetric cardiac imaging data. A patient specific 4D computational model is generated based on one or more of personalized geometry, material properties, fluid boundary conditions, and flow velocity measurements in the 4D geometric model. Patient specific material properties of the aortic wall are estimated based on the 4D geometrical model and the 4D computational model. A patient specific biomechanical model can be generated based on Fluid Structure Interaction (FSI) simulations using the 4D computational model and the estimated material properties of the aortic wall. Patient specific clinical parameters can be extracted based on the 4D geometric model and the FSI simulations. Disease progression modeling and risk stratification can be performed based on the patient specific clinical parameters.

These and other advantages of the invention will be apparent to those of ordinary skill in the art by reference to the following detailed description and the accompanying drawings.

BRIEF DESCRIPTION OF THE DRAWINGS

FIG. 5 illustrates exemplary models of the heart chambers and the aortic valve;

FIGS. 6A and 6B illustrate integrating individual models to generate a personalized anatomical heart model;

FIG. 7 illustrates exemplary results of a multi-component, patient specific heart models;

DETAILED DESCRIPTION

Figure 1:
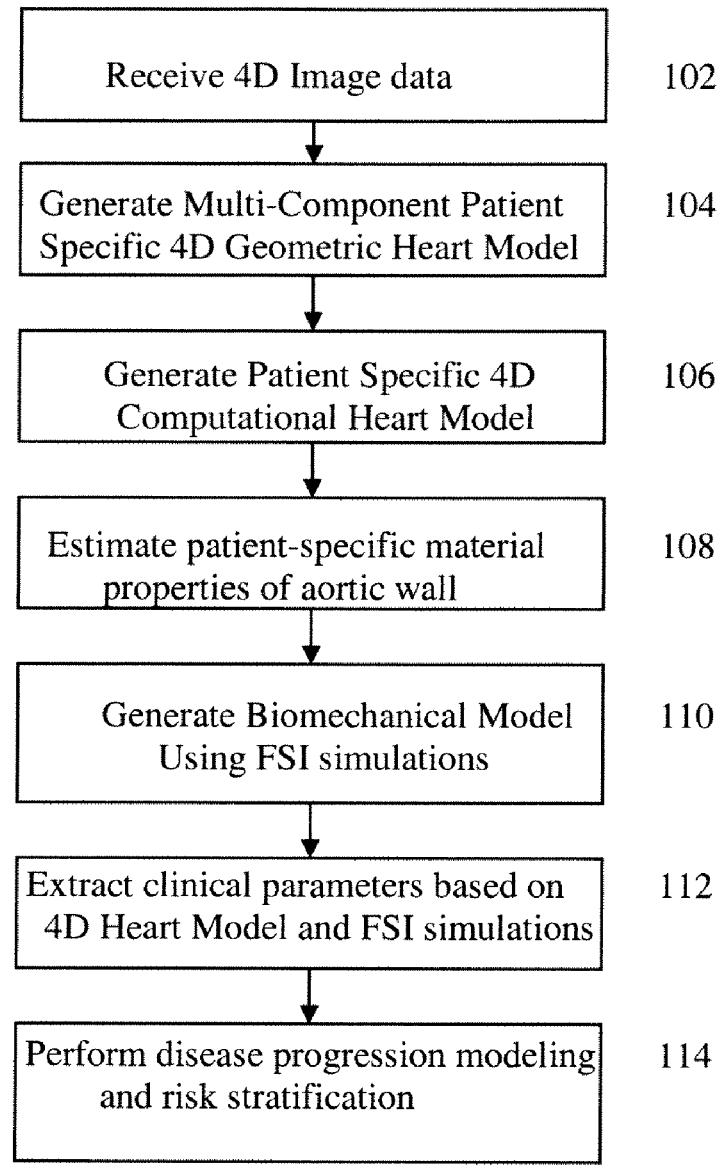
FIG. 1 illustrates a method for multi-component heart and aorta modeling and cardiac disease decision support according to an embodiment of the present invention.

The present invention relates to generating a 4D personalized anatomical model of the heart from a sequence of volumetric data, such as computed tomography (CT), magnetic resonance imaging (MRI), and echocardiography data. Such sequences of volumetric data also referred to herein as 4D image data or 4D images, are sequences taken over a period of time to cover one or more cardiac cycles, in which each frame is a 3D image (volume). Embodiments of the present invention are described herein to give a visual understanding of the heart modeling method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention are directed to generating a comprehensive and personalized computational model of the full heart and aorta from high resolution CT, MR, and rotational X-ray imaging, in order to guide decision support for patient evaluation, risk stratification, procedure planning, and timing of surgical intervention. Subtle, but critical interconnections are estimated between the aorta and the heart's components and disease progression models are derived. In order for the underlying hemodynamic analysis to generate patient-specific parameters to be subsequently used as discriminative features for the decision support process, embodiments of the present invention include the following components:

(1) patient-specific geometric models and the corresponding blood flow velocity fields of the aorta, aortic valve, and left ventricle;

(2) a non-linear, anisotropic, parametric, constitutive model for the mechanical properties of the aortic wall;

(3) parameter estimation of the wall model by solving the underlying optimization problem that seeks to minimize the error in the residue between the aortic wall displacement as determined from the imaging data and the displacement obtained by Fluid Structure Interaction (FSI) simulations with the patient-specific velocity boundary conditions and geometry (from 3D-time resolved PC MRI, CT, and rotational C-ray imaging);

(4) advanced anatomic, physiological, and hemodynamic parameters derived from the simulations of patient specific models; and (5) disease progression models for cardio-vascular disease to predict the risk of specific conditions.

As described herein, complete personalized modeling of left ventricle, aortic valve, and aorta using advanced computational techniques for coupled fluid and solid mechanics and parameter estimation in conjunction with rich imaging (e.g., CT, MR, Rotational X-ray) allows discovery and testing of practical decision support algorithms for improved management and early detection of cardiac diseases in individual patients. Successful personalized modeling of cardiac disease provides practical support for the complex surgical decision process with the goal of decreasing morbidity and mortality. The identification of risk models allows appropriate timing of surgical intervention, validates the efficacy of current medical therapy, and provides insight into the design of new therapies.

Figure 2:
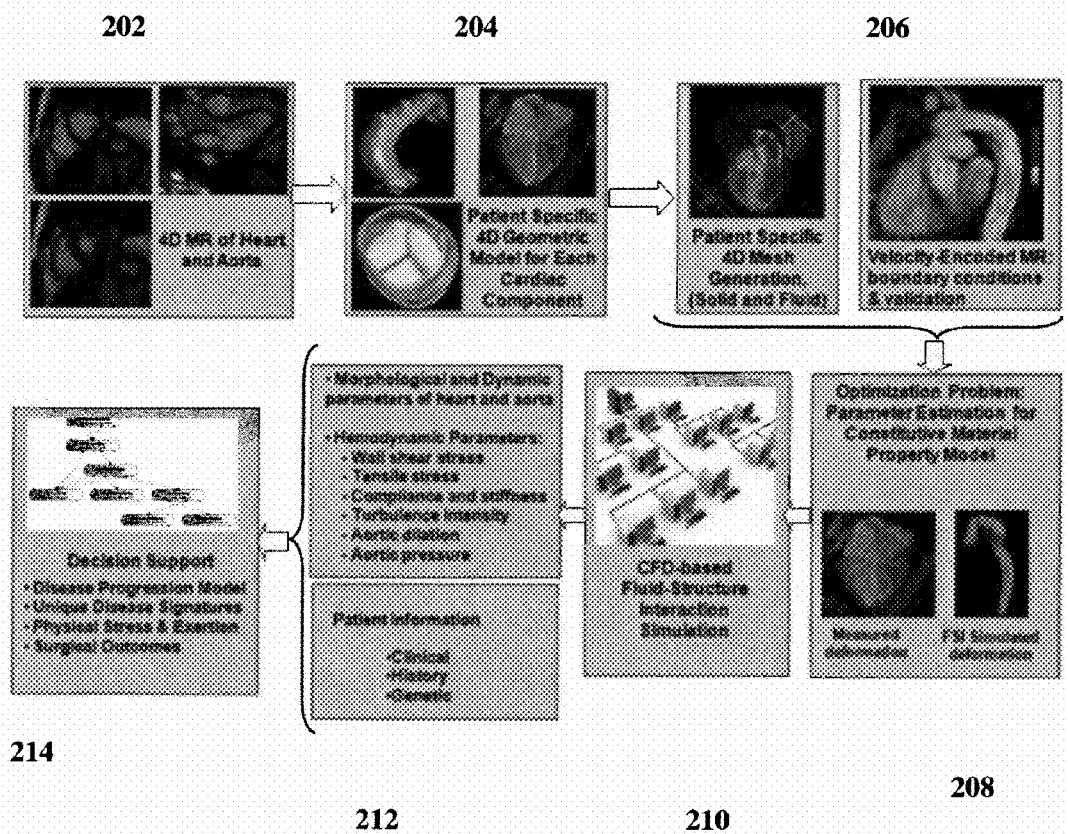
FIG. 2 illustrates an example of the multi-component hear and aorta modeling and decision support method of FIG. 1 according to an embodiment of the present invention.

FIG. 1 illustrates a method for multi-component heart and aorta modeling and cardiac disease decision support according to an embodiment of the present invention. The method of FIG. 1 transforms image data representing a coronary region of a patient into an anatomical model of the heart and uses the heart model for decision support in diagnosing and treating cardiac disease. FIG. 2 illustrates an example of the multi-component hear and aorta modeling and decision support method of FIG. 1 according to an embodiment of the present invention.

Referring to FIG. 1, at step 102, 4D image data is received. In particular, at least one sequence of volumetric image data is received. The sequence of volumetric image data can be a sequence of 3D images (volumes) acquired over a certain time period. For example, such a 4D image data (3D+time) can be acquired over a one full heart cycle. One or more sequences can be received using various medical imaging modalities. For example, according to various embodiments of the present invention, 4D CT data, 4D echocardiography, and 4D magnetic resonance (MR) image data can be received, as well as other types of image data. The image data can be received directly from one or more image acquisition devices, such as a CT scanner, an ultrasound device, or an MR scanner. It is also possible that previously stored image data be loaded, for example from a memory or storage of a computer system or some other computer readable storage medium. As illustrated in FIG. 2, 4D MR data is received at step 202.

Returning to FIG. 1, at step 104, a multi-component patient-specific 4D geometric model is estimated from the received 4D image data. In particular, a 4D geometric model is generated from the received image data for each of multiple cardiac components, such as the aorta, aortic valve, mitral valve, tricuspid valve, pulmonary valve, and left and right ventricles and atria. As illustrated in FIG. 2, at step 204, patient specific 4D geometric heart models are generated for each cardiac component.

Figure 3:
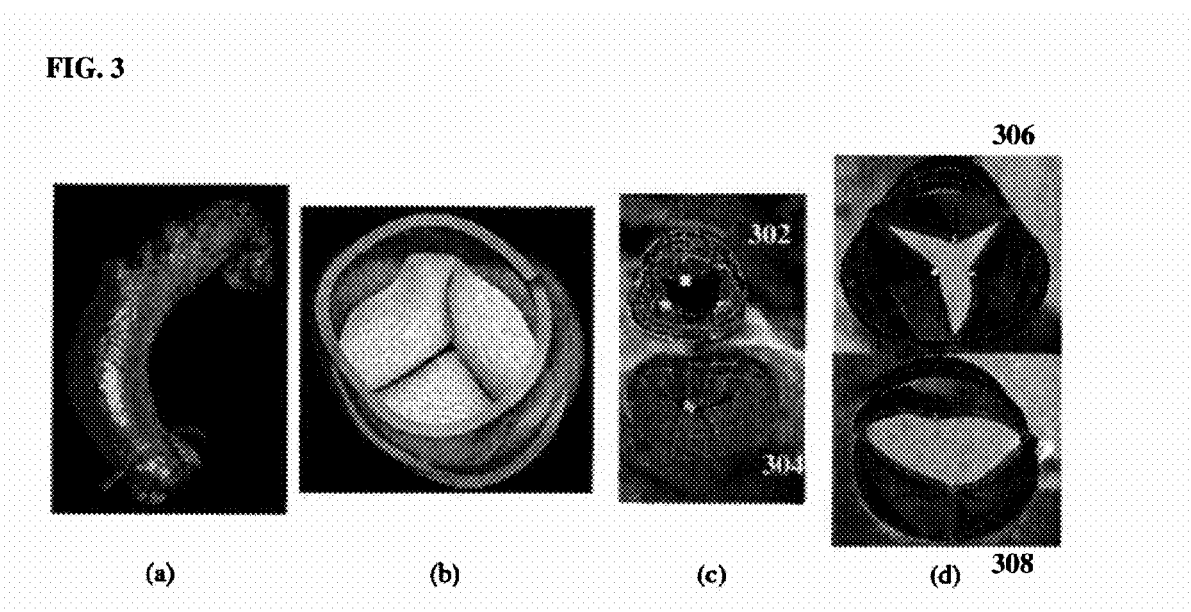
FIG. 3 illustrates exemplary patient-specific models generated for cardiac components from received image data.

FIG. 3 illustrates exemplary patient-specific models generated for cardiac components from received image data. As illustrated in FIG. 3, image (a) shows a patient-specific model of the aorta and the ostia derived from CT data. Image (b) shows a patient specific model of the aortic valve generated from transesophageal echocardiogram (TEE) data. Image (c) shows a patient specific model of coupled aortic (302) and mitral (304) valves generated from TEE data. Image (d) shows a patient specific model of pathological aortic valves. In particular, image (d) shows a stenotic aortic valve 306 and a bicuspid aortic valve 308.

Figure 4:
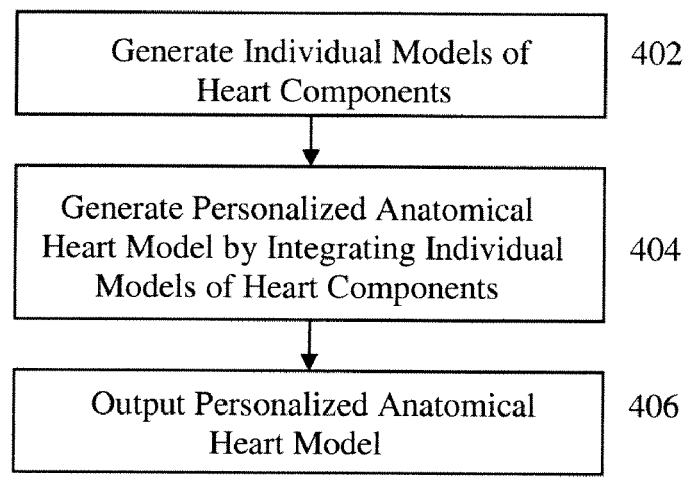
FIG. 4 illustrates a method for generating a 4D personalized geometric model of the heart according to an embodiment of the present invention.

The multi-component 4D geometric model gives the morphology of the patient's heart and can be used to determine morphological (dimensions) and dynamic parameters for any component of the heart. For example, the patient specific 4D geometric model can be used to measure the left ventricle (LV) volume and ejection fraction (EF), inter-chamber synchronicity analysis, aortic and mitral valve analysis, etc. FIG. 4 illustrates a method for generating a 4D personalized geometric model of the heart according to an embodiment of the present invention. The method of FIG. 4 transforms image data representing a coronary region of a patient to generate a personalized geometric model of the heart for that patient. The method of FIG. 4 can be used to implement step 104 of the method of FIG. 2.

At step 402, an individual model is generated from the received image data for each of a plurality of heart components. According to an embodiment of the present invention, models are generated for the heart chambers: left ventricle (LV) (endocardium and epicardium), right ventricle (RV), left atrium (LA) and right atrium (RA); valves: mitral valve and aortic valve; and main vessels: aorta and pulmonary trunk. All of these portions of the heart are referred to herein collectively as the "heart components". For each heart component, a physiological model of the heart component is estimated in each frame of the 4D image data using a discriminative database-guide estimation/detection technique.

The physiological model of each anatomic structure (heart component) is constructed offline prior to generating the personalized heart model for a particular patient. Each physiological model is generated based on a mathematical representation of the corresponding heart component in a set of annotated training data. For example, the physiological model for each heart component can be generated using mean shapes of the heart component in a set of annotated training data. For example, United States Patent Application Publication No. 2008/0101676, which is incorporated herein by reference, describes a generating a four-chamber physiological heart model and fitting the heart model to image data. As described therein, the heart model is a 3D mesh and initial meshes for each chamber are generated using mean shapes of the chambers in annotated training data. Further, United States Patent Application No. 2009/0123050, which is incorporated herein by reference, describes a 4D physiological model of the aortic valve. A physiological model can similarly be generated offline for each of the heart components based on a set of annotated training data.

In order to estimate a physiological model of a particular heart component in a 3D image (i.e., frame of a 4D image sequence), the parameters of the physiological model are estimated to fit the image using a discriminative machine-learning technique based on a large database of annotated training images. According to one embodiment, marginal space learning (MSL) is used to localize the physiological model in each of the images.

The idea of MSL is not to learn a classifier directly in a full similarity transformation parameter space, but to incrementally learn discriminative classifiers in increasing dimensionality based on annotated training data. As the dimensionality increases, the valid (positive) space region becomes more restricted by previous marginal space classifiers. In order to estimate a physiological model of an anatomic structure, such as a particular heart component, in an image, the estimation of the similarity transformation (i.e., position, orientation, and scale) corresponding to the location of the heart component can be split into three stages: position estimation, position-orientation estimation, and full similarity transformation estimation. A discriminative classifier is trained for each stage based on the training data. All of the discriminative classifiers can be trained as Probabilistic Boosting Trees (PBTs). In addition to reducing the size of the search space, another advantage of MSL is that it is possible to use different features, such as 3D Haar features or steerable features to train the classifier in each marginal space level.

Examples of estimating physiological models of various heart components in 3D image data using MSL are described in the following publications, the disclosures of which are incorporated herein by reference: United States Patent Application Publication No. 2008/0101676, describes estimating a model for each chamber of the in 3D CT image data; United States Patent Application No. 2009/0123050, describes fitting a physiological model of the aortic valve to 4D CT data; and Yang et al., "3D Ultrasound Tracking of the Left Ventricles Using One-Step Forward Prediction and Data Fusion of Collaborative Trackers", CVPR 2008, describes fitting a model of the left ventricle to a sequence of 3D ultrasound images. It is to be understood that each of the heart components can be estimated by fitting a physiological model of the heart component to image data using discriminative machine-learning techniques, similarly to the above examples.

Once the parameters of each individual heart component model are estimated in each frame of the 4D image data, e.g., using MSL, learning-based boundary detection can be performed on the individual heart component model in each image to refine the estimated model parameters. In particular, the boundary of each estimated model can be refined using the learning-based boundary detection to increase the accuracy of the physiological model estimation for each heart component.

FIG. 5 illustrates exemplary models of the heart chambers and the aortic valve. As illustrated in FIG. 5 image 510 shows the LV endocardium 501, the LV epicardium 502, the RV 503, the LA 504, and the RA 505 in diastole and image 520 shows the LV endocardium 501, the LV epicardium 502, the RV 503, the LA 504, and the RA 505 in systole. Image 530 shows the aortic valve 506 in diastole and image 540 shows the aortic valve 506 in systole.

Returning to FIG. 4, at step 404, a 4D personalized anatomical model of the heart is generated by integrating the individual models generated for each of the heart components. Each of the individual heart component models resulting from step 402 is a mesh made of a certain number of points. According to an advantageous implementation, in order to integrate the individual models of the LV (endocardium and epicardium), RV, LA, RA, mitral valve, aortic valve, aorta, and pulmonary trunk, mesh point correspondences are established between connecting or overlapping models. The mesh point correspondences allow the models to be correctly aligned with respect to each other. It is possible to establish mesh point correspondence between models by re-sampling the models. For example, United States Patent Application Publication No. 2008/0262814, which is incorporated herein by reference, describes various re-sampling methods to establish mesh point correspondence between models of the four heart chambers in order to correctly align the heart chamber models. It is to be understood that the techniques described in United States Patent Application Publication No. 2008/0262814 can be extended to establish mesh point correspondence between the individual heart component models described herein.

FIGS. 6A and 6B illustrate integrating individual models to generate a personalized anatomical heart model. The images of FIG. 6A illustrate a possible order for integrating the heart component models according to an embodiment of the present invention. As illustrated in FIG. 6A, image 602 shows an LV endocardium model 601. Image 604 shows the integration of the mitral valve model 603. Image 606 shows the integration of the LV epicardium model 605. Image 608 shows the integration of the aortic valve model 607 and the aortic root model 609. Image 610 shows the integration of the RV model 611. Image 612 shows the integration of the LA model 613. Image 614 shows the integration of the RA model 615. Image 616 shows the integration of the aorta model 617. Image 618 shows the integration of the pulmonary trunk model 619. As illustrated in FIG. 4B, images 620 and 622 show 3D renderings of the resulting personalized anatomical heart model fit to image data. It is to be understood that although FIGS. 6A and 6B, illustrate the integration of the heart component models for a 3D volume, the heart component models can be similarly integrated in each frame of a 4D image sequence.

Returning to FIG. 4, at step 406, the 4D personalized anatomical heart model is output. The 4D personalized anatomical heart model can be output by storing the 4D personalized anatomical heart model to a memory, storage, or computer readable medium. The 4D personalized anatomical heart model can also be output by displaying the 4D personalized anatomical heart model or printing an image of the 4D personalized anatomical heart model. The output 4D personalized anatomical heart model can be used for further medical image processing. For example, the 4D personalized anatomical heart model can be used to estimate various morphological and functional measurements, of the heart. The 4D personalized anatomic heart model can also be used to simulate blood flow or blood-tissue interaction. FIG. 7 illustrates exemplary results of a multi-component, patient specific heart models. As illustrated in FIG. 7, image (a) shows left and right ventricles and the aortic root derived from MR data. Image (b) shows the left endocardium and epicardium, right ventricle, left and right atria, and the aortic root derived from CT data. Image (c) shows all of the above components plus the aorta derived from CT data.

Returning to FIG. 1, at step 106, a patient-specific 4D computational model based on personalized geometry, material properties, fluid boundary conditions, and flow velocity measurements (e.g., velocity encoded contrast MR and echo Doppler) in the 4D geometric model is generated. For example, measurements of a chamber's volume and a valve's opening area computed over a full cardiac cycle enable for the characterization of the hemodynamics. Blood quantity, pressure and velocity can be directly estimated, for each of the four chambers, from the fitted 4D personalized anatomical heart model. The integration of Doppler echocardiogram or velocity encoded contrast MR velocity measurements further enhances the robustness of the blood parameter computation. Referring to FIG. 2, at step 206, the patient-specific 4D mesh is generated and velocity encoded contrast MR is generated at the aortic and mitral valve.

Returning to FIG. 1, at step 108, patient-specific material properties of the aortic wall are estimated. In order to perform realistic patient-specific simulations for determining the hemodynamic and wall mechanics parameters, an accurate representation is needed of the material properties of the aortic wall, in conjunction with measured velocity boundary conditions at the inlet and outlet of the aortic valve, measured velocity boundary conditions at the outlet of the aorta, and blood pressure measurements.

In order to estimate the patient-specific material properties of the aortic wall, a parameter estimation procedure is used. Since the aortic wall is a three-layered structure with inhomogeneous mechanical properties, a non-linear, hyperelastic constitutive multi-fiber model can be used for the aortic wall. Under this formulation, the aortic wall is modeled as a four-fiber family model, which takes into consideration the effect of the isotropic elastin behavior in addition to the anisotropic collagen behavior. In such a model of the aortic wall, the additive strain energy is given by:

$$\psi = \psi_{iso} + \psi_{aniso}, \quad (1)$$

where $\psi$, the strain energy is composed of an anisotropic part $\psi_{aniso}$ due to the multiple fiber families, together with an isotropic neo-hookean term $\psi_{iso}$, as shown below:

$$\psi_{iso} = c(I_1 - 3) \quad (2)$$

$$\Psi_{aniso} = \sum_{k=1}^{4} \frac{c_1^{(k)}}{4c_2^{(k)}} \left( \exp\left[ c_2^{(k)} (\lambda^{(k)2} - 1)^2 \right] - 1 \right), \quad (3)$$

where $I_1$ is the first invariant of the right Cauchy-Green tensor C (i.e., $I_1$=trace(C)) and c, $c_1^{(k)}$, $c_2^{(k)} \leq 0$ are material parameters. $\lambda^{(k)}$ is the stretch of the $k^{th}$ fiber family, given by:

$$\lambda^{(k)} = \sqrt{(\lambda_\theta \sin\alpha^{(k)})^2 + (\lambda_z \cos\alpha^{(k)})^2}, \quad (4)$$

with $\alpha^{(k)}$ being the orientation and $\lambda_\theta$, $\lambda_z$ being the circumferential and axial stretches, respectively.

The unknown coefficients c, $c_1^{(k)}$, $c_2^{(k)}$ are determined using a parameter estimation procedure in conjunction with Fluid Structure Interaction (FSI) based simulations. The time-resolved geometric models obtained in step 104 are used for determining the actual (measured) deformation of the aortic wall due to pulsatile blood flow during the cardiac cycle. A parametric model of the material property is then used together with the time resolved in-flow out-flow velocity profile measured by 3D CINE MRI acquisition to perform a fully couple two-way FSI based simulation for the blood flow across the aortic wall and the length of the aorta.

The parameter estimation procedure is modeled as an optimization problem where the underlying objective function is the residue (or error) between the actual (measured) deformation of the aortic wall and the simulated deformation of the aortic wall. The objective function can be expressed as:

$$r(c) = \frac{1}{N} \sum_{i=1}^{N} \| d_i^{FSI}(c) - d_i^{MRI} \|, \quad (5)$$

where r(c) denotes the residue, and $d_i^{FSI}(c)$ and $d_i^{MRI}$ denote the simulated and measured deformation vectors of the wall, respectively, at the N sample points (indexed by i). The unknown parameters (characterizing the material properties of the aortic wall) constitute the parameter vector $c = [c, c_1^{(k)}, c_2^{(k)}]$ for k=1, 2, 3, and 4.

Figure 8:
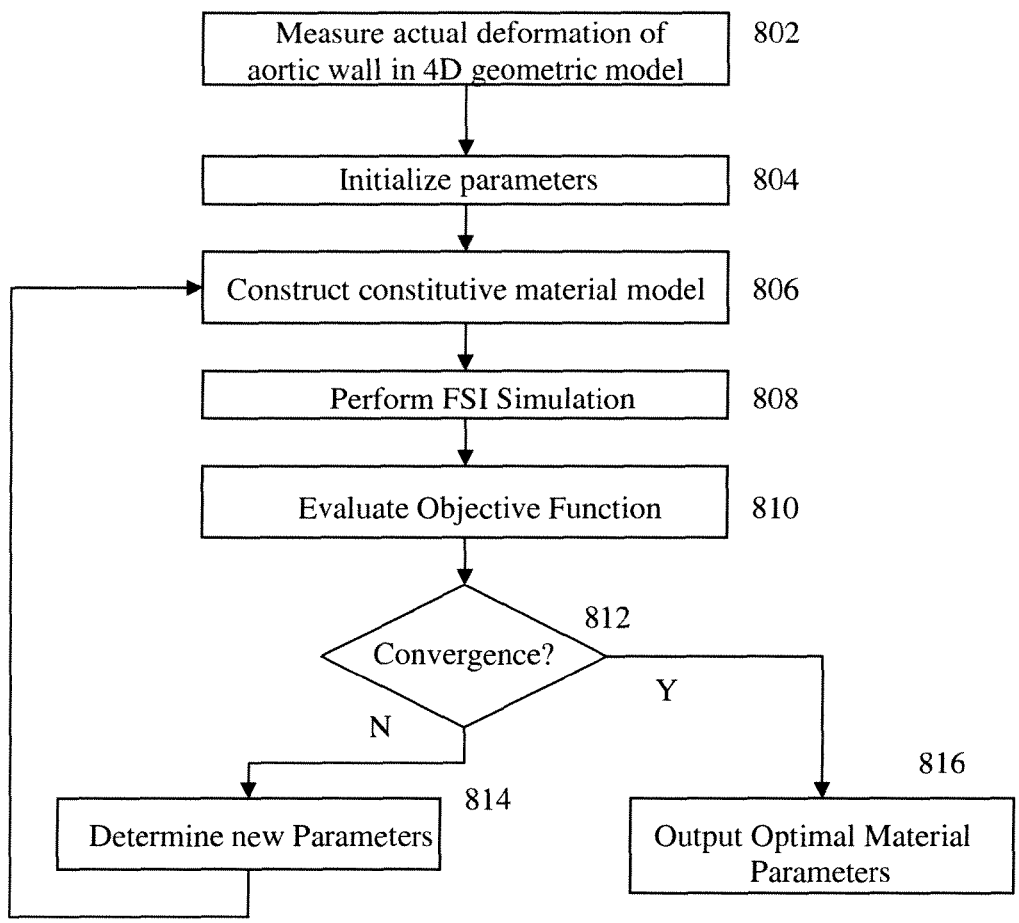
FIG. 8 illustrates a method for estimating parameters that characterize the material properties of the aorta wall according to an embodiment of the present invention.

FIG. 8 illustrates a method for estimating parameters that characterize the material properties of the aorta wall according to an embodiment of the present invention. The method of FIG. 8 is used to estimate the parameters c, $c_1^{(k)}$, $c_2^{(k)}$ described above. The method of FIG. 8 can be used to implement step 108 of FIG. 1.

As illustrated in FIG. 8, at step 802, an actual deformation of the aortic wall is measured in the patient-specific 4D geometric model. For example, the actual deformation of the aortic wall due to pulsatile blood flow during the cardiac cycle is measured in the 4D geometric model. This deformation may be measured at multiple sampling points resulting in a measured deformation vector.

At step 804, the parameters are initialized. According to an advantageous implementation, initial estimates for the parameters can be selected from the literature in order to speed up the optimization process. For example, average values of a large population can be used for the initial parameter values.

At step 806, a constitutive material model of the aortic wall is constructed with the current parameters. The constitutive material model of the aortic wall has a strain energy determined as described above in Equations (1)-(4) based on the current parameters.

At step 808, an FSI based simulation is performed using the constitutive material model of the aortic wall with the current parameters. For example, the constitutive material model can be used together with the time resolved in-flow out-flow velocity profile measured by 3D CINE MRI acquisition to perform a fully couple two-way FSI based simulation for the blood flow across the aortic wall and the length of the aorta. The FSI simulation results in a simulated blood flow and simulated deformation of the aortic wall.

At step 810, the objective function is evaluated based on the FSI based simulation results. For example, the residue (error) between the current simulated deformation and the measured deformation can be calculated (Equation (5)). Although the objective function described above in Equation (5) compares the simulated and measures deformations of the aortic wall, the present invention is not limited thereto. It is also possible to compare velocity vectors from simulated flow resulting from the FSI based simulation with velocity vectors determined from the patient-specific model.

At step 812, it is determined whether the objective function has converged. According to an advantageous implementation, the objective function has converged when the calculated residue (error) is less than a predetermined threshold value. If it is determined that the objective function has not converged, the method proceeds to step 814. If it is determined that the objective function has converged, the method proceeds to step 816.

At step 814, new parameters are determined using an optimization algorithm. For example, new parameters can be determined by minimization of the objective function (with respect to the material parameter vector c) using a non-linear gradient based optimization algorithm, such as the well-known Levenberg-Marquardt algorithm, which utilizes gradient information to obtain a locally optimal solution. Once new parameters are determined, the method returns to step 806. Steps 806-814 are then repeated until the objective function converges.

At step 814, the optimal material parameters are output. Accordingly, when it is determined that the objective function has converged, the current parameters are determined to be the optimum material parameters for the aortic wall, and the optimal material parameters are output. The optimum material parameters give an accurate representation of the material properties of the aortic wall and can be used in patient-specific simulations for determining hemodynamics and wall mechanics.

This parameter estimation for estimating parameters that characterize material properties of the aortic wall can subsequently be used to resolve the mechanical properties of the vascular wall material on a fine mesh, and to generate a 'map' of the varying material properties along the aorta.

Returning to FIG. 1, at step 110, a patient specific biomechanical model is generated based on Fluid Structure Interaction (FSI) simulations using the 4D computational model and the estimated patient-specific material properties of the aortic wall. A detailed simulation of the blood flow pattern of the patient, as well as the interaction of the blood with the anatomical structures of the heart, can be obtained by combining the above described measurements with established biomechanical and hemodynamics models, and finite element methods. For example, using FSI techniques the blood flow and tissue interaction can be simulated using the parameters measured in the computational model. This enables the computation of path, pressure, and velocity of the blood on a particle level with a desired granularity. If material properties are not measured in the computational model FSI can be specialized to computational fluid dynamics (CFD) in order to obtain full blood flow simulation using only the patient specific dynamic geometry, without simulating interaction of the blood and the tissue.

In order to derive patient-specific anatomic and hemodynamic features from the computational models and use them subsequently for the identification of relevant risk factors and disease-progression models, a comprehensive simulation approach can be utilized. In addition to generating hemodynamic attributes for the decision support framework, the computational model is used as a tool for non-invasive assessment of surgical procedures on specific patients and for analyzing the effect of surgery on key parameters like wall shear stress and displacement. This is achieved by appropriately modifying the patient-specific structure model (e.g., to reflect surgical changes) together with the boundary conditions, and then simulating the blood flow in the simulated post-operative heart and aorta. At the same time, operational models can also be used to simulate physical stress and exertion conditions, to analyze its effect on the key hemodynamic attributes, and to incorporate it into the risk progression model to generally reflect the activity of daily living.

Once the patient-specific material property map is established, a coupled FSI simulation of the left ventricle, aortic valve, and the aorta can be performed with patient-specific velocity boundary conditions and time-resolved geometry (from 3D-time resolved PC MRI, Ct, and Rotational X-ray imaging). FSI methods can be tailored to the particular heart parts, as some parts perform an active role (e.g., ventricle) or a mixed passive/active role (e.g., valves, arteries). Exemplary FSI methods for various heart parts are described below.

Figure 9:
FIG. 9 illustrates an exemplary wall shear stress distribution in the aorta, resulting from a patient-specific simulation.

Aorta (or other blood vessels): FSI models that include both fluid and structure equations fully coupled together through a set of boundary conditions, such as equal displacement, equal traction, and no-slip condition. An Arbitrary Lagrangian Eulerian (ALE) formulation can be used for the coupled problem. This allows advanced bio-mechanical measurements including but not limited to wall shear stress, elasticity or stiffness, Von-Mises stress, flow pathlines, streamlines, and vorticity throughout the length of the aorta. FIG. 9 illustrates an exemplary wall shear stress distribution in the aorta, resulting from a patient-specific simulation.

Heart Chambers: Hemodynamic model based on Navier-Stokes equations and rigid structure assumption driven by moving boundary conditions associated with i) heart walls contractions/displacement during both diastolic and systolic cycled and ii) dynamic blood flow velocity/pressure boundary conditions at the flow entry and exit points.

Figure 10:
FIG. 10 illustrates exemplary results of a CFD based FSI simulation for an aortic valve.

Heart Valves: Immersed Boundary Method treating structures as parts as fluid with forces added to modify the Navier-Stokes equations and no-slip boundary condition. FIG. 10 illustrates exemplary results of a CFD based FSI simulation for an aortic valve.

In the example of FIG. 2, at step 210, CFD-based FSI simulation is performed on the patient-specific computational models.

Returning to FIG. 1, at step 112, patient-specific clinical parameters are extracted based on the patient-specific model and the FSI simulations. In particular, phenotypic, anatomic and hemodynamic parameters are derived from the patient-specific model and the simulations. The personalized models enable direct quantification of morphological, dynamical, and bio-mechanical characteristics including: dilation of the entire length of the thoracic aorta including the aortic annulus, and sino-tubular junction, aortic arch, proximal and distal descending aorta; chamber size and mass; vessel wall thickness; luminal dilation and aortic compliance and stiffness by calculation of relations between change in segmental aortic diameters or volumes and central blood pressure. CFD simulations on the patient-specific anatomic models generate hemodynamic parameters that characterize the complex flow fields including turbulence, jets, and recirculation. These simulations can further be used to derive the wall shear stress, blood velocity flow field, wall displacement, wall Von Mises stress (tensile), and turbulence intensity (vorticity). As illustrated in FIG. 2, at step 212, morphological and dynamic parameters of the heart and aorta are extracted, as well as hemodynamic parameters including wall shear stress, tensile stress, compliance and stiffness, turbulence intensity, aortic dilation, and aortic pressure. Additional patient information (e.g., clinical, history, and genetic information) can also be input and used as parameters.

At step 114, patient-specific disease progression and risk stratification is performed based on the patient-specific phenotypic, anatomic, and hemodynamic parameters derived from the patient-specific 4D model and the FSI simulations. The disease progression and risk stratification are performed using a trained decision-support model. To support decision-making, multi-level Markov Cycle tree models can be used for both disease progression and risk stratification as a function of time. Individual patients are characterized and stratified based on their patient-specific dynamic heart model. Markov models for decision analysis provide a rich framework for integrating available patient information, stimulating disease progression based on time-dependent patient risk, and providing statistics of expected outcomes based on alternatives. According to a possible implementation, the models can be studies under various conditions, such as normal operation, after simulated surgical intervention, and under simulated stress conditions.

This stratification is reflected by differences in transition rates among disease states, as well as transition rates from each disease state to critical states. It can be performed using methods of cluster analysis and automated subgroup discovery. Traditional statistical methods, such as multivariate regression and significance tests, can be combined with modern machine learning methods, such as Support Vector Machines, SCR's, Probabilistic Boosting Trees, and Bayesian Networks. Predictive models enable the identification of individual risk factors, as well as combinations of characteristics that together are most strongly associated with patient outcomes, even if individually they are not predicative. As illustrated in FIG. 2, at step 214, decision support is performed based on the extracted parameters using a disease progression model. The disease progression model can reflect unique genetic disease signatures, physical stress and exertion, and various possible surgical outcomes. Heart specific disease progression and risk stratification is described in greater detail below.

Disease Progression Modeling: Disease progression can be modeled in terms of the continuous evolution and temporal fluctuations of the anatomic, morphological, hemodynamic and phenotype parameters extracted at step 110. At a particular time (t), the condition of an individual patient can be characterized in terms of the instantaneous values of variables that will constitute the present state of an individual patient (x(t)). Each patient is represented as a distinct point in a state-space, a high-dimensional space spanned by the various attributes of the patients, which completely defines the state. The state vector contains both continuous and discrete state variables, some of which are inherently inter-related with one another due to the various biological, physical, and physiological constraints. These are observed, measured, extracted from imaging studies, or simulated under patient-specific framework, as described above.

Disease progression is manifested in the state dynamics, which represents continuous progression of the disease and discontinuous discrete events of intervention therapies. This is represented as follows:
$\dot{x}(t) = \Phi^i(x(t), w(t))$, $i \in I = \{1, 2 \ldots N\}$, where $\Phi^i$ is the dynamics of the progression after the treatment i, trajectory x(t) defines the temporal progression of the disease, while the discrete state i(t) represents the broader changes that model the treatment or other sudden changes. i(t) can take on a finite set of values, determined by its dynamics $i(t) = \phi(i^-(t), x(t))$, and w(t) represents the external effects.

Figure 11:
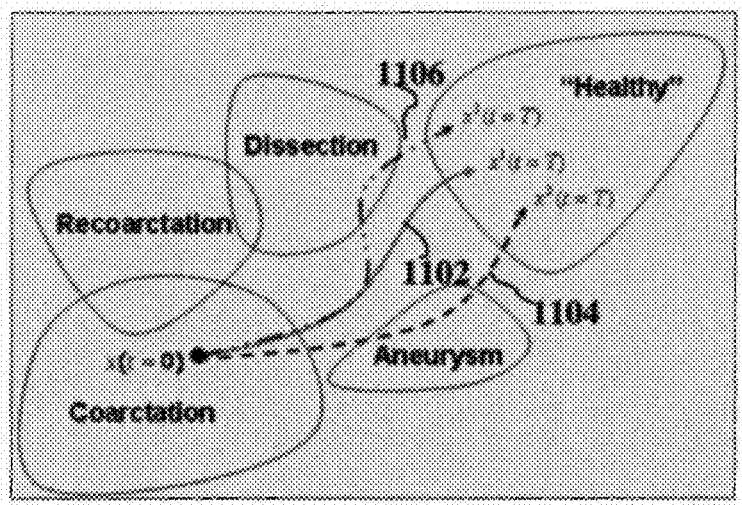
FIG. 11 illustrates disease progression trajectories for coarctation.

FIG. 11 illustrates disease progression trajectories for coarctation. As illustrated in FIG. 11, the trajectories 1102, 1104, and 1106 represents disease trajectories under different interventions/treatments. As shown in FIG. 11, each trajectory 1102, 1104, and 1106 begins in coarctation and ends with the patient being healthy. FIG. 11 also shows complications or dissection, aneurysm, and recoarctation that the trajectories 1102, 1104, and 1106 can pass through. According to an embodiment of the present invention, in order to determine the progression trajectories, a non-linear similarity measure is learned and then used to distinguish specific patient groups. This is done by integrating measurements of morphology, dynamics, hemodynamics, material properties, phenotype and therapeutic procedures, obtained at multiple phases along the clinical workflow (i.e. pre-intervention and subsequent follow-ups). Hence, each patient profile is represented as a multi-dimensional vector of features. From the comprehensive set of quantities, we isolate individual patients in classes, specific to the clinical use cases for a particular cardiovascular disease. The probability that classifies patients in clinical relevant disease progression clusters is learned from equivalence constraints, able to capture statistics from heterogeneous input measurements. Non-linear regression is applied to estimate the probability, which models a similarity measure between a pair of two patient profiles. During clinical decision-making, the profile of the subject patient is compared to each individual in the training population, while the k-Nearest Neighbor algorithm applied on the similarity scores performs the classification.

Risk Stratification: Risk stratification involves characterizing the risk for intra- or post-procedural complications for individual patients. Our proposed methodology involves applying a non-linear similarity measure to distinguish between two classes: low-risk patients and high-risk patients. The classification is performed separately for each type of complication associated with the particular cardiovascular disease of interest (e.g. in case of coarctation, the three complications are dissection, aneurysm and recoarctation). To distinguish between low- and high profiles, we integrate the measurements obtained during the clinical evaluation at stage (morphology, dynamics, hemodynamics, phenotype and material properties). Additionally, the feature vector used for classification contains parameters of specific therapies to be applied (e.g. surgery, percutaneous implant etc). The similarity measure is learned from patients that are pre-classified in low or high risk, based on their follow-up studies.

Figure 12:
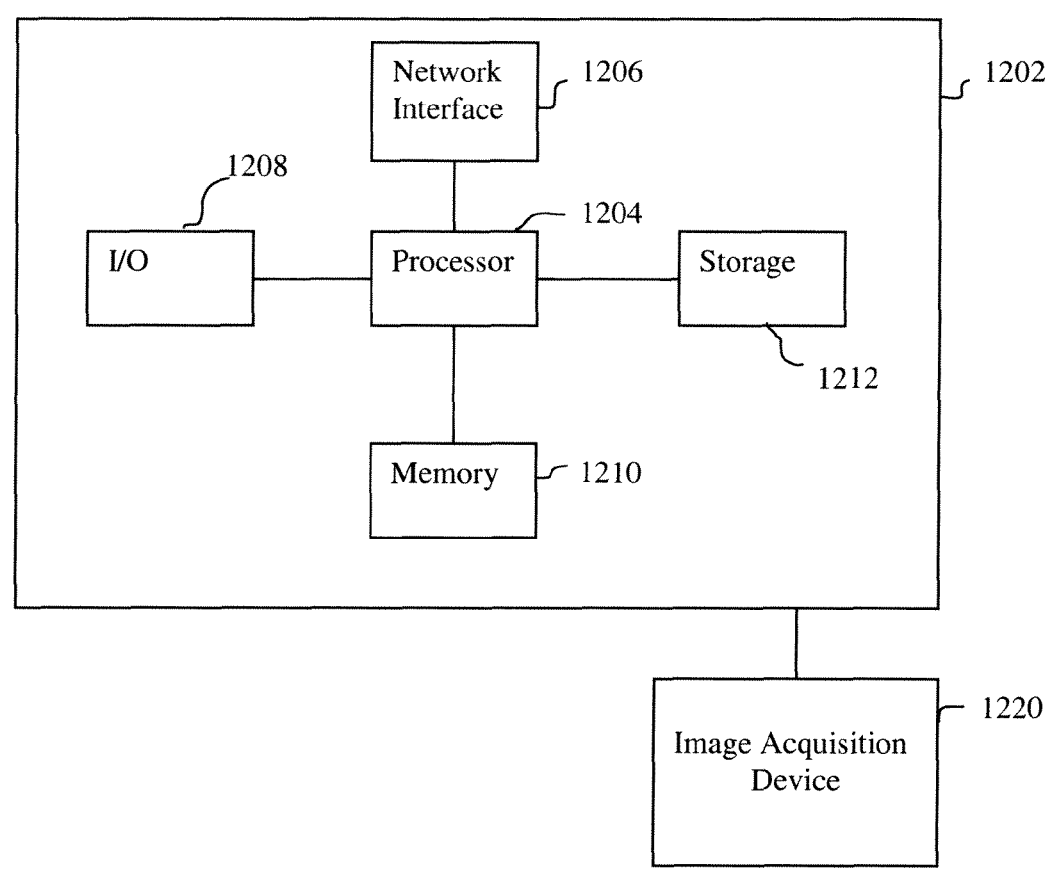
FIG. 12 is a high-level block diagram of a computer capable of implementing the present invention.

The above-described methods for generating a personalized anatomic model of the heart and performing disease progression modeling and risk stratification may be implemented on a computer using well-known computer processors, memory units, storage devices, computer software, and other components. A high-level block diagram of such a computer is illustrated in FIG. 12. Computer 1202 contains a processor 1204, which controls the overall operation of the computer 1202 by executing computer program instructions which define such operation. The computer program instructions may be stored in a storage device 1212 (e.g., magnetic disk) and loaded into memory 1210 when execution of the computer program instructions is desired. Thus, the steps of the method of FIGS. 1, 2, 4, and 8 may be defined by the computer program instructions stored in the memory 1210 and/or storage 1212 and controlled by the processor 1204 executing the computer program instructions. At least one image acquisition device 1220, such as a CT scanning device, ultrasound device, MR scanning device, etc., can be connected to the computer 1202 to input the 3D volumes to the computer 1202. It is possible to implement the image acquisition device 1220 and the computer 1202 as one device. It is also possible that the image acquisition device 1220 and the computer 1202 communicate wirelessly through a network. The computer 1202 also includes one or more network interfaces 1206 for communicating with other devices via a network. The computer 1202 also includes other input/output devices 1208 that enable user interaction with the computer 1202 (e.g., display, keyboard, mouse, speakers, buttons, etc.). Such input/output devices 1208 may be used in conjunction with a set of computer programs as an annotation tool to annotate volumes received from the image acquisition device 1220. One skilled in the art will recognize that an implementation of an actual computer could contain other components as well, and that FIG. 12 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

What is claimed is:

1. A method for multi-component heart modeling and cardiac disease decision support, comprising:
   generating a multi-component patient specific 4D geometric model of the heart and aorta estimated from a sequence of volumetric cardiac imaging data of a patient generated using at least one medical imaging modality;
   generating a patient specific 4D computational model based on one or more of personalized geometry, material properties, fluid boundary conditions, and flow velocity measurements in the 4D geometric model; and
   estimating patient specific material properties of an aortic wall using the 4D geometrical model and the 4D computational model by determining parameters of a constitutive material model of the aortic wall to minimize a residue between a simulated deformation of the aortic wall determined based on a Fluid Structure Interaction (FSI) simulation and a measured deformation of the aortic wall in the 4D geometric model.

2. The method of claim 1, wherein the constitutive material model of the aortic wall comprises a non-linear, hyperelastic constitutive multi-fiber model.

3. The method of claim 1, wherein said step of estimating patient specific material properties of an aortic wall using the 4D geometrical model and the 4D computational model comprises:
   (a) determining a measured deformation of the aortic wall in the 4D geometric model;
   (b) initializing parameters that characterize material properties of the aortic wall;
   (c) constructing a constitutive material model of the aortic wall using current values of the parameters;
   (d) performing a Fluid Structure Interaction (FSI) simulation using the constitutive material model to determine a simulated deformation of the aortic wall;
   (e) evaluating an objective function that calculates a residue between the simulated deformation and the measured deformation;
   (f) determining whether the objective function has converged;
   (g) if the objective function has not converged, determining new values of the parameters and repeating steps (c)-(f); and
   (h) if the objective function has converged determining that the current values of the parameters are optimum values.

4. The method of claim 3, wherein step (a) comprises:
   measuring a deformation of the aortic wall due to pulsatile blood flow during a cardiac cycle at a plurality of sampling points using the 4D geometric model.

5. The method of claim 3, wherein step (b) comprises:
   initializing the parameters using average parameter values for a population.

6. The method of claim 3, wherein the constitutive material model of the aortic wall models strain energy of the aortic wall.

7. The method of claim 3, wherein step (e) comprises:
   performing a fully coupled two-way FSI simulation for blood flow across the aortic wall and over the length of the aorta using the constitutive material model together with a time resolved in-flow out-flow velocity profile determined based on the 4D computational model.

8. The method of claim 3, wherein step (f) comprises:
   determining that the objective function has converged if the residue between the simulated deformation and the measured deformation is less than a threshold.

9. The method of claim 3, wherein step (g) comprises:
   determining new values of the parameters that locally optimize the objective function.

10. The method of claim 1, further comprising:
    generating a patient specific biomechanical model based on Fluid Structure Interaction (FSI) simulations using the 4D computational model and the estimated material properties of the aortic wall.

11. The method of claim 10, further comprising:
    extracting patient specific clinical parameters based on the 4D geometric model and the FSI simulations; and
    performing disease progression modeling and risk stratification based on the patient specific clinical parameters.

12. An apparatus for multi-component heart modeling and cardiac disease decision support, comprising:
    means for generating a multi-component patient specific 4D geometric model of the heart and aorta estimated from a sequence of volumetric cardiac imaging data of a patient generated using at least one medical imaging modality;
    means for generating a patient specific 4D computational model based on one or more of personalized geometry, material properties, fluid boundary conditions, and flow velocity measurements in the 4D geometric model; and
    means for estimating patient specific material properties of an aortic wall using the 4D geometrical model and the 4D computational model comprising:
       means for determining parameters of a constitutive material model of the aortic wall to minimize a residue between a simulated deformation of the aortic wall determined based on a Fluid Structure Interaction (FSI) simulation and a measured deformation of the aortic wall in the 4D geometric model.

13. The apparatus of claim 12, wherein said means for determining parameters of a constitutive material model of the aortic wall to minimize a residue between a simulated deformation of the aortic wall determined based on a Fluid Structure Interaction (FSI) simulation and a measured deformation of the aortic wall in the 4D geometric model comprises:
    means for determining a measured deformation of the aortic wall in the 4D geometric model;
    means for initializing parameters that characterize material properties of the aortic wall;
    means for constructing a constitutive material model of the aortic wall using current values of the parameters;
    means for performing a Fluid Structure Interaction (FSI) simulation using the constitutive material model to determine a simulated deformation of the aortic wall;
    means evaluating an objective function that calculates a residue between the simulated deformation and the measured deformation;
    means for determining whether the objective function has converged; and means for determining new values of the parameters.

14. The apparatus of claim 13, wherein said means for determining a measured deformation of the aortic wall in the 4D geometric model comprises:
   means for measuring a deformation of the aortic wall due to pulsatile blood flow during a cardiac cycle at a plurality of sampling points using the 4D geometric model.

15. The apparatus of claim 13, wherein said means for performing a Fluid Structure Interaction (FSI) simulation using the constitutive material model to determine a simulated deformation of the aortic wall comprises:
   means for performing a fully coupled two-way FSI simulation for blood flow across the aortic wall and over the length of the aorta using the constitutive material model together with a time resolved in-flow out-flow velocity profile determined based on the 4D computational model.

16. The apparatus of claim 13, wherein said means for determining new values of the parameters comprises:
   means for determining new values of the parameters that locally optimize the objective function.

17. The apparatus of claim 12, further comprising:
   means for generating a patient specific biomechanical model based on Fluid Structure Interaction (FSI) simulations using the 4D computational model and the estimated material properties of the aortic wall.

18. The apparatus of claim 17, further comprising:
   means for extracting patient specific clinical parameters based on the 4D geometric model and the FSI simulations; and
   performing disease progression modeling and risk stratification based on the patient specific clinical parameters.

19. A non-transitory computer readable medium encoded with computer executable instructions for multi-component heart modeling and cardiac disease decision support, the computer executable instructions defining steps comprising:
   generating a multi-component patient specific 4D geometric model of the heart and aorta estimated from a sequence of volumetric cardiac imaging data of a patient generated using at least one medical imaging modality;
   generating a patient specific 4D computational model based on one or more of personalized geometry, material properties, fluid boundary conditions, and flow velocity measurements in the 4D geometric model; and
   estimating patient specific material properties of an aortic wall using the 4D geometrical model and the 4D computational model by determining parameters of a constitutive material model of the aortic wall to minimize a residue between a simulated deformation of the aortic wall determined based on a Fluid Structure Interaction (FSI) simulation and a measured deformation of the aortic wall in the 4D geometric model.

20. The computer readable medium of claim 19, wherein the computer executable instructions defining the step of estimating patient specific material properties of an aortic wall using the 4D geometrical model and the 4D computational model comprise computer executable instructions defining the steps of:
   (a) determining a measured deformation of the aortic wall in the 4D geometric model;
   (b) initializing parameters that characterize material properties of the aortic wall;
   (c) constructing a constitutive material model of the aortic wall using current values of the parameters;
   (d) performing a Fluid Structure Interaction (FSI) simulation using the constitutive material model to determine a simulated deformation of the aortic wall;
   (e) evaluating an objective function that calculates a residue between the simulated deformation and the measured deformation;
   (f) determining whether the objective function has converged;
   (g) if the objective function has not converged, determining new values of the parameters and repeating steps (c)-(f); and
   (h) if the objective function has converged determining that the current values of the parameters are optimum values.

21. The computer readable medium of claim 20, wherein the computer executable instructions defining step (a) comprise computer executable instructions defining the step of
   measuring a deformation of the aortic wall due to pulsatile blood flow during a cardiac cycle at a plurality of sampling points using the 4D geometric model.

22. The computer readable medium of claim 20, wherein the computer executable instructions defining step (e) comprise computer executable instructions defining the step of:
   performing a fully coupled two-way FSI simulation for blood flow across the aortic wall and over the length of the aorta using the constitutive material model together with a time resolved in-flow out-flow velocity profile determined based on the 4D computational model.

23. The computer readable medium of claim 20, wherein the computer executable instructions defining step (g) comprise computer executable instructions defining the step of:
   determining new values of the parameters that locally optimize the objective function.

24. The computer readable medium of claim 20, further comprising computer executable instructions defining the step of:
   generating a patient specific biomechanical model based on Fluid Structure Interaction (FSI) simulations using the 4D computational model and the estimated material properties of the aortic wall.

25. The computer readable medium of claim 24, further comprising computer executable instructions defining the steps of:
   extracting patient specific clinical parameters based on the 4D geometric model and the FSI simulations; and
   performing disease progression modeling and risk stratification based on the patient specific clinical parameters.

* * * * *